US00PP07894P

United States Patent [19]

Marciel

[11] Patent Number: Plant 7,894

[45] Date of Patent: Jun. 30, 1992

[54] MINIATURE ROSE PLANT NAMED DEVDICHA

[75] Inventor: Stanley G. Marciel, Aptos, Calif.

[73] Assignee: DeVor Nurseries, Inc., Watsonville, Calif.

[21] Appl. No.: 615,154

[22] Filed: Nov. 19, 1990

[51] Int. Cl.[5] ..... A01H 5/00
[52] U.S. Cl. ..... Plt./7
[58] Field of Search ..... Plt. 7

[56] References Cited

U.S. PATENT DOCUMENTS

P.P. 7,637 9/1991 Marciel ..... Plt. 7

*Primary Examiner*—James R. Feyrer
*Attorney, Agent, or Firm*—Charles W. Rummler

[57] ABSTRACT

A new and distinct rose plant of small compact size particularly adapted for culture in a 4 in. pot and distinguished by its continuous and profuse production of small red-margined flowers carried on strong upright stems at a height of about 13 cm. from the last flower cut, the plant itself being a round compact bush having a free branching growth habit with small but abundant foliage.

1 Drawing Sheet

BACKGROUND OF THE NEW PLANT

This new rose plant originated as a seedling hybrid resulting from the crossing of an unknown seedling with pollen from a plant named 'Scarlet Sunblaze' (unpatented) at my nursery at Watsonville, Calif. This particular seedling having been selected by me for propagation because of its vigorous growth habit, small compact size and profuse production of well balanced flowers of a pleasing color and propagation was done by met at Watsonville by means of cuttings with such pleasing success that such propagation was continued through several successive generations at Watsonville which demonstrated conclusively that the novel characteristics of this plant would hold true from generation to generation and appeared to be firmly fixed.

DESCRIPTION OF THE DRAWING

This new pot rose plant is illustrated by the accompanying full color photographic drawings of which the right hand view shows a mature potted plant of this variety illustrating buds and flowers in a full range of development from unopened bud to a fully developed bloom; and the left hand view shows the various parts of the flowering plant from unopened bud to a face view of a mature flower and including parts of the foliage, the color rendition of both the right and left hand drawing views being as nearly true to that herein specifed as is possible to obtain by conventional photographic procedures.

DESCRIPTION OF THE NEW VARIETY

The following is a detailed description of my new pot plant rose based upon observation of greenhouse plants at Watsonville and with the color designations according to The R.H.S. Colour Chart published by The Royal Horticultural Society of London, England.

THE PLANT

Origin: Seedling.
Parentage:

*Seed parent.*—An unknown seedling.
*Pollen parent.*—The variety 'Scarlet Sunblaze' (unpatented).

Classification:
*Botanic.*—Miniature rose plant.
*Commercial.*—Miniature pot rose.

Form: Small compact bush.
Growth habit: Vigorous and upright.
Height: About 130 mm. from last flower cut.
Branching character: Free branching.
Foliage: Of small size and abundant.
*Number of leaves.*—From 3 to 7.
*Size.*—About 23 mm. long and 13 mm. wide.
*Leaflets.*—Number: Varying from 3 to 7. Size: About 12 mm. long and 8 mm. wide. Shape: Acute with denticulate margins. Texture: Leathery. Aspect: Smooth and glossy. Color: Upper side— Yellow Green 147-A. Under side— Yellow Green 147-B. Rachis: About 20 mm. for 3 part leaf and about 35 mm. for a 7 part leaf. Pedioles: About 6 mm. long.
Ribs and veins: Depressed on upper side and rounded on lower side.
Thorns: Declining.
*Color.*—Greyed Orange 177-D.
*Size.*—4 mm.

THE BUD

Size: Small mini-flora.
*Diameter.*—About 13 mm.
*Length.*—About 16 mm.
Form: Slender, tapering and pointed.
Rate of opening: Slow.
Color of petals:
*When sepals first divide.*—Red Purple 58-B.
*When petals begin to unfurl.*—Red Purple 61-B.
Sepals:
*Shape.*—Spreading.
*Number.*—5.
*Character.*—Hooded over the bud and when the flowers open, the sepals stand up.

*Color.*—Inside — Yellow Green 147-B with White hairs nearing the center. Outside — Yellow Green 146-B.

Calyx:

*Shape.*—Funnel-shaped.

*Size.*—Medium in breadth and length.

*Aspect.*—Smooth.

*Splitting.*—The calyx does not split.

Peduncle of flower stem: Hairy and about 41 mm. long.

*Character.*—Slender and erect.

*Color.*—Yellow Green 146-A.

THE FLOWER

Blooming habit: Continuous and profuse the year around blooming freely under greenhouse conditions.

Size of bloom: Medium.

*Diameter.*—(When about ¾ open) 42 mm. by 39 mm.

*Depth.*—13 mm.

Borne: Singly.

Shape:

*When bloom first opens.*—Cup shaped with high center.

*When bloom matures.*—Nicely imbricated.

Petalage:

*Number.*—37.

*Number of florets.*—11.

*Arrangement.*—Imbricated.

*Form.*—Pointed spoon shaped with pointed apex.

*Margin.*—Slightly ruffled.

*Texture.*—Soft.

*Aspect.*—Velvety.

*Color.*—Outer petals: Margins — Red Purple 60-B and Red Purple 61-B with Yellow White 158-C at the base. Reverse side — Greyed Purple 187-B with Red Purple 60-B. Base — Red 36-D.

*Petaloids.*—Number: 11. Size: About 9 mm. Color: Margins — Red Purple 61-C and base of Green White 157-C.

Peduncle:

*Length.*—38 mm.

*Color.*—Yellow Green 146-A.

*Character.*—Upright and sturdy.

Discoloration after full bloom: Slightly.

Persistence: The flower hangs on and dries.

Disease resistance: Moderately resistant to mildew, rust and black spots as observed at Watsonville, Calif.

Fragrance: Mild.

Lasting quality: Long lasting on plant and as a cut flower.

THE REPRODUCTIVE ORGANS

Stamens:

*Number.*—82.

*Arrangement.*—Slightly introrse.

*Anthers.*—Size: 2 mm. Color: Yellow Orange 22-B.

*Filaments.*—Length: 6 mm. Color: Greyed Purple 186-B and Greyed Green 194-C.

*Pollen.*—Color: Yellow Orange 22-B.

Pistils:

*Number.*—55.

*Styles.*—Length: 10 mm. Color: Greyed Green 193-B with Greyed Purple 185-D at the tip.

*Stigmas.*—Color: Red 49-D.

Character of the ovaries: Long, slender and oblong with covering of silvery hairs.

I claim:

1. The new and distinct variety of rose plant of the miniature pot rose type, substantially as herein shown and described, particularly characterized by its profuse and continuous production of red-margined flowers on the strong stems of a small compact plant having abundant foliage.

* * * * *

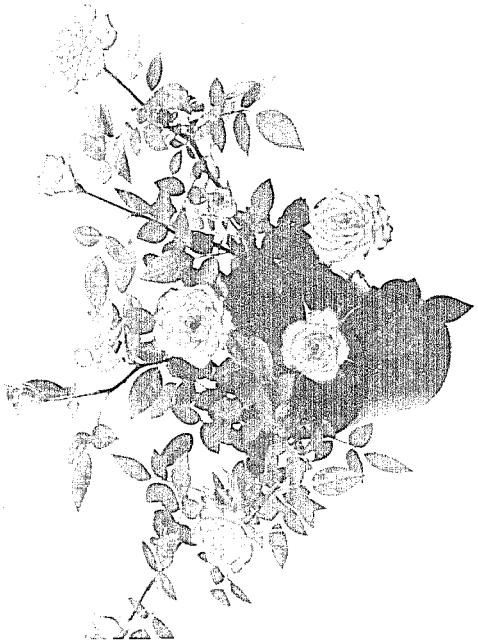
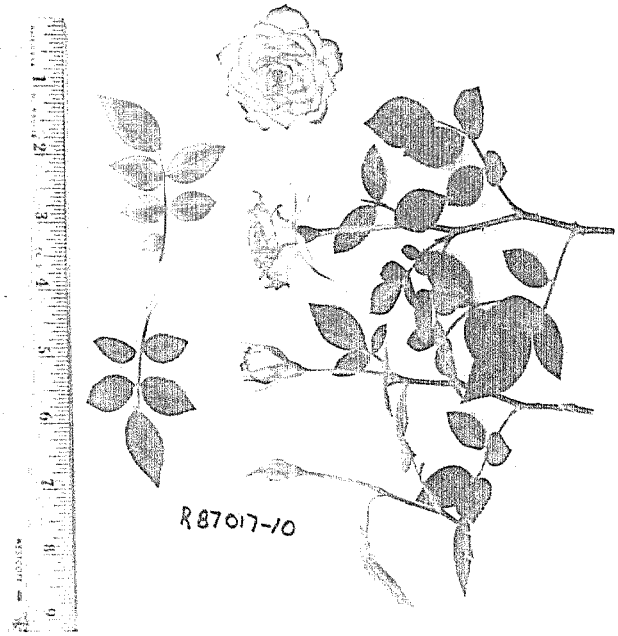
R87017-10